(12) United States Patent
Nokihara et al.

(10) Patent No.: US 7,091,175 B2
(45) Date of Patent: Aug. 15, 2006

(54) ANGIOGENESIS DRUGS

(76) Inventors: Kiyoshi Nokihara, 7-115, Fuujiyama-cho, Misasagi, Yamashina-ku, Kyoto-shi, Kyoto 607-8422 (JP); Yoshinosuke Hamada, 2-8, Miyukicho, Higashiosaka-shi, Osaka 579-8057 (JP); Nariaki Matsuura, 2-2-1, Yugecho, Yao-shi, Osaka 581-0032 (JP); Junzo Takahashi, 19-D-714, Mihogaoka, Ibaraki-shi, Osaka 567-0047 (JP)

( * ) Notice: Subject to any disclaimer, the term of this patent is extended or adjusted under 35 U.S.C. 154(b) by 0 days.

(21) Appl. No.: 10/491,418

(22) PCT Filed: Oct. 2, 2002

(86) PCT No.: PCT/JP02/10278

§ 371 (c)(1),
(2), (4) Date: Jun. 1, 2004

(87) PCT Pub. No.: WO03/030925

PCT Pub. Date: Apr. 17, 2003

(65) Prior Publication Data

US 2004/0266696 A1    Dec. 30, 2004

(30) Foreign Application Priority Data

Oct. 2, 2001    (JP) ............................. 2001-306201

(51) Int. Cl.
*A01N 37/18*    (2006.01)
(52) U.S. Cl. .......................................................... 514/2
(58) Field of Classification Search ..................... None
See application file for complete search history.

(56) References Cited

U.S. PATENT DOCUMENTS 6,509,026 B1 *    1/2003    Ashkar et al. ............... 424/422

FOREIGN PATENT DOCUMENTS

| JP | 2000-300263 A | 10/2000 |
| WO | WO 91/05802 A1 | 5/1991 |
| WO | WO 99/08730 A1 | 2/1999 |
| WO | WO 00/63236 A2 | 10/2000 |
| WO | WO 01/71358 A1 | 9/2001 |

OTHER PUBLICATIONS

Mogi, et al., Circulation, 2000, 102, 65.*
Yokosaki, et al., The Journal of Biological chemistry, 1999, 274, 36328-34.*
Smith, et al., Experimental Cell Research, 1998, 242, 351-360.*
Myles, et al., Journal of Biomaterials Science, 2000, 11, 69-86.*
Kiyoshi Nokihara et al.; Peptide Science 2000: T. Shioiri (Ed.); The Japanese Peptide Society (2001); pp. 373-376.
Masayuki Okazaki et al.; Dentistry in Japan; vol. 37; Mar. 2001; pp. 95-100.

* cited by examiner

*Primary Examiner*—Bruce R. Campell
*Assistant Examiner*—Satyanarayana R. Gudibande
(74) *Attorney, Agent, or Firm*—Birch, Stewart, Kolasch & Birch, LLP

(57) ABSTRACT

A novel angiogenesis drug which can be clinically used for therapies of human or the like is disclosed. The angiogenesis drug according to the present invention comprises a peptide as an effective component, which has a prescribed amino acid sequence and has an angiogenesis action.

20 Claims, No Drawings

SEQUENCE LISTING

<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<223> OTHER INFORMATION: Oligopeptide having angiogenic activity -continued

```
<400> SEQUENCE: 1

Ser Val Val Tyr Gly Leu Arg
 1               5

<210> SEQ ID NO 2
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 2

Ala Val Val Tyr Gly Leu Arg
 1               5

<210> SEQ ID NO 3
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 3

Ser Ala Val Tyr Gly Leu Arg
 1               5

<210> SEQ ID NO 4
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 4

Ser Val Ala Tyr Gly Leu Arg
 1               5

<210> SEQ ID NO 5
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 5

Ser Val Val Tyr Ala Leu Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 6

Ser Val Val Tyr Gly Ala Arg
 1               5

<210> SEQ ID NO 7
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 7
```

Ser Val Val Tyr Gly Leu Ala
 1               5

<210> SEQ ID NO 8
<211> LENGTH: 7
<212> TYPE: PRT
<213> ORGANISM: Artificial Sequence
<220> FEATURE:
<223> OTHER INFORMATION: Oligopeptide not having angiogenic activity

<400> SEQUENCE: 8

Ser Val Val Ala Gly Leu Arg
 1               5

<210> SEQ ID NO 9
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 9

Ser Val Val Phe Gly Leu Arg
 1               5

<210> SEQ ID NO 10
<211> LENGTH: 6
<212> TYPE: PRT
<213> ORGANISM: Artificial Sequence
<220> FEATURE:
<223> OTHER INFORMATION: Oligopeptide having angiogenic activity

<400> SEQUENCE: 10

Ser Val Val Tyr Gly Leu
 1               5

<210> SEQ ID NO 11
<211> LENGTH: 6
<212> TYPE: PRT
<213> ORGANISM: Artificial Sequence
<220> FEATURE:
<223> OTHER INFORMATION: Oligopeptide having angiogenic activity

<400> SEQUENCE: 11

Val Val Tyr Gly Leu Arg
 1               5

<210> SEQ ID NO 12
<211> LENGTH: 8
<212> TYPE: PRT
<213> ORGANISM: Artificial Sequence
<220> FEATURE:
<223> OTHER INFORMATION: Oligopeptide having angiogenic activity

<400> SEQUENCE: 12

Ser Val Val Tyr Gly Leu Arg Gly
 1               5

<210> SEQ ID NO 13
<211> LENGTH: 11
<212> TYPE: PRT
<213> ORGANISM: Artificial Sequence
<220> FEATURE:
<223> OTHER INFORMATION: Oligopeptide having angiogenic activity

<400> SEQUENCE: 13

```
Gly Arg Gly Asp Ser Val Val Tyr Gly Leu Arg
  1               5                  10
```

<210> SEQ ID NO 14
<211> LENGTH: 8
<212> TYPE: PRT
<213> ORGANISM: Artificial Sequence
<220> FEATURE:
<223> OTHER INFORMATION: Oligopeptide having angiogenic activity

<400> SEQUENCE: 14

```
Arg Gly Asp Ser Val Val Tyr Gly
  1               5
```

<210> SEQ ID NO 15
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 15

```
Ser Val Val Tyr Gly Leu Arg
  1               5
```

<210> SEQ ID NO 16
<211> LENGTH: 7
<212> TYPE: PRT
<213> ORGANISM: Artificial Sequence
<220> FEATURE:
<223> OTHER INFORMATION: Oligopeptide having angiogenic activity

<400> SEQUENCE: 16

```
Ser Val Val Trp Gly Leu Arg
  1               5
```

<210> SEQ ID NO 17
<211> LENGTH: 5
<212> TYPE: PRT
<213> ORGANISM: Artificial Sequence
<220> FEATURE:
<223> OTHER INFORMATION: Oligopeptide having angiogenic activity

<400> SEQUENCE: 17

```
Ser Val Val Tyr Gly
  1               5
```

<210> SEQ ID NO 18
<211> LENGTH: 4
<212> TYPE: PRT
<213> ORGANISM: Artificial Sequence
<220> FEATURE:
<223> OTHER INFORMATION: Oligopeptide having angiogenic activity

<400> SEQUENCE: 18

```
Ser Val Val Tyr
  1
```

<210> SEQ ID NO 19
<211> LENGTH: 3
<212> TYPE: PRT
<213> ORGANISM: Artificial Sequence
<220> FEATURE:
<223> OTHER INFORMATION: Oligopeptide not having angiogenic activity

<400> SEQUENCE: 19

```
Ser Val Val
  1
```

```
<210> SEQ ID NO 20
<211> LENGTH: 5
<212> TYPE: PRT
<213> ORGANISM: Artificial Sequence
<220> FEATURE:
<223> OTHER INFORMATION: Oligopeptide not having angiogenic activity

<400> SEQUENCE: 20

Val Tyr Gly Leu Arg
 1               5

<210> SEQ ID NO 21
<211> LENGTH: 4
<212> TYPE: PRT
<213> ORGANISM: Artificial Sequence
<220> FEATURE:
<223> OTHER INFORMATION: Oligopeptide not having angiogenic activity

<400> SEQUENCE: 21

Tyr Gly Leu Arg
 1

<210> SEQ ID NO 22
<211> LENGTH: 3
<212> TYPE: PRT
<213> ORGANISM: Artificial Sequence
<220> FEATURE:
<223> OTHER INFORMATION: Oligopeptide not having angiogenic activity

<400> SEQUENCE: 22

Gly Leu Arg
 1
```

US 7,091,175 B2

ANGIOGENESIS DRUGS

TECHNICAL FIELD

The present invention relates to an angiogenesis drug having an action to newly generate blood vessels. The angiogenesis drug according to the present invention is useful for not only therapies of ischemic diseases, but also for regeneration and repair of organs using biological substitute materials such as artificial bones.

BACKGROUND ART

A considerably high mortality rate in Japan is caused by ischemic diseases due to vascular occlusion, such as myocardial infarction and cerebral infarction. There are also another ischemic diseases which are not fatal but deteriorate QOL (quality of life), such as aortic obstructive diseases for which amputation of lower extremity is forced. To overcome these ischemic diseases, angiogenesis therapy by which sufficient circulation is supplied through newly generated blood vessels is hoped very much. Angiogenesis plays an important role not only in the treatments of ischemic diseases, but also in the adaptation of biomaterials. Some artificial biomaterials including apatite and titanium have been used for filling bone defect or implant. These artificial biomaterials have poor compatibilities with the surrounding soft and hard tissues, so that they often cannot exhibit their primary function well.

To improve the compatibility with the surrounding soft and hard tissues, it has been proposed to use peptide derivatives having bio-adhesive functions. For example, it has been proposed to use a composite as an artificial bone, which is a mixture of apatite carbonate having the composition and crystallinity similar to those of hard tissue in the body, and collagen which is one of the bio-adhesive functions (K. Nokihara et al., The Japanese Peptide Society, Osaka, 373–376, 2001., Development of Biomimetic Materials: Novel Composite Material Carrying Immobilized Functional Peptides; M. Okazaki et al., Dentistry in Japan, 37, 95–100, 2001, A New Concept of CO3 apatite-Collagen Composites with Adhesion Motif as Biomaterials). This composite has a good biocompatibility and is a promising biomimetic artificial bone.

If blood vessels are newly formed on the surfaces and insides of such biomaterials, nutrients and oxygen are sufficiently supplied to the cells on the surfaces and insides of the transplanted biomaterials by means of abundant blood at an early stage after surgery, so that optimum environment for the cells to function is formed, thereby advantageously attaining good taking of the materials to the body.

On the other hand, peptides which have great advantages in the safeties in view of side effects, metabolic properties and the like, are easy to design, and highly efficient synthesis methods and characterization methods have been established. In addition, amino acid derivatives are convenient building units for the construction of combinatorial chemical libraries, and optimization thereof can be attained by solid phase synthesis methods in a short time. Thus, it is advantageous that peptides having a relatively low molecular weight and exhibiting angiogenic activities, which may improve interactions between biomaterials and the surrounding soft and hard tissues, may be synthesized and administrated alone or conjugates, that is, such peptides are immobilized onto biomaterials. However, low molecular peptides or peptide-mimetic organic compounds having prominent angiogenic activities are scarcely known.

DISCLOSURE OF THE INVENTION

Accordingly, an object of the present invention is to discover a peptide having angiogenesis action and to provide a novel angiogenesis drug which may be clinically used for human therapeutics or the like.

The present inventors intensively studied to discover that peptides having specific amino acid sequences have angiogenic activities to complete the present invention.

That is, the present invention provides an angiogenesis drug comprising as an effective ingredient a peptide having the amino acid sequence shown in SEQ ID NO:1 or a peptide having the same amino acid sequence as shown in SEQ ID NO:1 except that 1 to 3 amino acids are substituted, and/or 1 or 2 amino acids located at one or both termini, respectively, of said sequence are deleted, and/or that other amino acid(s) is(are) attached to one or both termini of said sequence, which has an angiogenesis action.

By the present invention, peptides having strong angiogenic activities were discovered, and novel angiogenesis drugs containing the peptides as effective ingredients were first provided. The angiogenesis drugs according to the present invention are useful for regeneration and repair of organs using biological substitute materials such as artificial bones, and also for therapies of ischemic diseases such as myocardial infarction, cerebral infarction and obstructive aortic sclerosis, which occupies a large portion of lifestyle diseases.

MODES OF THE INVENTION

As will be concretely described in the Examples below, the present inventors discovered that the heptapeptide having the amino acid sequence shown in SEQ ID NO: 1 has an angiogenesis action. Therefore, in a preferred example of the angiogenesis drug according to the present invention, the angiogenesis drug comprises the heptapeptide having the amino acid sequence shown in SEQ ID NO: 1.

It is well known that, in general, a peptide having a physiological activity may retain its physiological activity even when one or more amino acids are substituted or deleted, or one or more amino acids are inserted or added to the amino acid sequence. Thus, peptides (hereinafter referred to as "modified peptides" for convenience) having the same amino acid sequence as shown in SEQ ID NO:1 except that 1 to 3 amino acids are substituted, and/or 1 or 2 amino acids located at one or both termini, respectively, of the sequence are deleted, and/or that other amino acid(s) is(are) attached to one or both termini of the sequence, which have angiogenic activities, are within the scope of the present invention. The amino acids contained in the "modified peptides" are not restricted to the amino acids constituting naturally occurring proteins, but include amino acids obtained by chemically modifying (e.g., attaching nitro group(s) or halogen(s) to the side chain) the naturally occurring amino acids. The amino acids may be D-amino acids. As concretely confirmed in the Examples below, the peptide having the same amino acid sequence as shown in SEQ ID NO:1 except that one amino acid at the N-terminal or the C-terminal of SEQ ID NO:1 is deleted, has an angiogenic activity comparable to the peptide having the amino acid sequence shown in SEQ ID NO:1, so that the peptides are preferred modes of the present invention. As will be concretely described in the Examples below, the angiogenesis action was lost by substituting the fourth amino acid tyrosine in SEQ ID NO:1 by alanine (SEQ ID NO:8). Therefore, the fourth amino acid tyrosine residue is thought to be important, and it is preferred not to make a substitution of tyrosine, by which the chemical structure of the side chain of the tyrosine is largely changed. However, those other than the naturally occurring L-tyrosine, such as D-tyrosine and substituted tyrosines in which halogen(s) or nitro group(s) is(are) attached to the phenol ring in the side chain of tyrosine, are usually designed in medicinal chemistry as tyrosine substitute, and it is known that the peptides having the D-tyrosine or a modified tyrosine often have stronger or comparable effects than or to the peptide having tyrosine. Further, it is thought that even if the tyrosine is substituted with another amino acid having an aromatic ring in its side chain (e.g., phenylalanine), similar effect is exhibited. In fact, as will be concretely described in the Examples below, it was confirmed that the peptide in which the fourth amino acid tyrosine is substituted by phenylalanine exhibits better effect. Therefore, among the modified peptides, preferred peptides include peptides having the same amino acid sequence as shown in SEQ ID NO:1 except that 1 or 2 amino acids are substituted, with the proviso that the fourth amino acid tyrosine residue is tyrosine residue or an amino acid having an aromatic ring in its side chain, and/or that one amino acid located at one or both termini, respectively, of the sequence is deleted, and/or that other amino acid(s) is(are) attached to one or both termini of the sequence, which have angiogenic activities. The term "amino acid having an aromatic ring" used herein is not restricted to a naturally occurring amino acid, but includes tyrosine derivatives and phenylalanine derivatives wherein the aromatic ring of the tyrosine or phenylalanine is substituted by at least one substituent selected from the group consisting of nitro, halogen, $C_1$–$C_5$ alkyl and $C_1$–$C_5$ acyl. In cases where the substituent(s) exist(s), the number of substituents on the aromatic ring, preferably benzene ring, is 1 to 5, preferably 1 to 3. The term "aromatic ring" means benzene ring or a condensed ring (which may be hetero rings) containing benzene ring, such as naphthalene ring, preferably benzene ring.

As will be concretely described in the Examples below, the present inventors discovered that the peptide having the amino acid sequence shown in SEQ ID NO:9, which is the same amino acid sequence as shown in SEQ ID NO:1, except that the fourth amino acid tyrosine is substituted by phenylalanine has a higher angiogenic activity than the peptide having the amino acid sequence shown in SEQ ID NO:1. It should be noted that phenylalanine is an amino acid having an aromatic ring (benzene ring) in its side chain. Thus, a preferred mode of the present invention includes angiogenesis drugs comprising a peptide having the amino acid sequence shown in SEQ ID NO:9 or a peptide having the same amino acid sequence as shown in SEQ ID NO:9 except that one amino acid located at one or both termini, respectively, of the sequence is deleted, or that other amino acid(s) is(are) attached to one or both termini of the peptide having the amino acid sequence shown in SEQ ID NO:9 or to one or both termini of the peptide having the same amino acid sequence as shown in SEQ ID NO:9 except that one amino acid located at one or both termini, respectively, of the sequence is deleted, which has an angiogenesis action.

Since the region having the angiogenesis action is contained in the amino acid sequence shown in SEQ ID NO:1, even if other arbitrary amino acid sequence(s) is(are) attached to one or both termini of the peptide having the amino acid sequence shown in SEQ ID NO:1, or to one or both termini of the modified peptide having the same amino acid sequence as shown in SEQ ID NO:1 except that a part of the amino acids is substituted or its terminal region(s) is(are) deleted, which has an angiogenesis action, the resulting peptide may have angiogenesis action. This is assumed from the fact that the cell-adhesion action of the cell-adhesive proteins such as fibronectin and laminin is exerted by the region having the sequence RGD consisting of only three amino acids or by the region having the sequence YIGSR consisting of only five amino acids. Thus, since the region having the angiogenic activity is contained in the amino acid sequence shown in SEQ ID NO:1, even if (a) long sequence(s) is(are) attached to one or both termini of the peptide having the amino acid sequence shown in SEQ ID NO:1, or to one or both termini of the modified peptide having the same amino acid sequence as shown in SEQ ID NO:1 except that a part of the amino acids is substituted or its terminal region(s) is(are) deleted, which has an angiogenesis action, the resulting peptide is thought to have angiogenesis action as long as the above-mentioned peptide region or the modified peptide region is exposed for carrying out the interaction. At present, since the spatial structure of an artificial peptide can easily be expected based on its primary sequence by using a commercially available computer software, a peptide with which the above-mentioned peptide region or the modified peptide region is exposed can easily be designed even if the size of the peptide is large.

Thus, there is no upper limit of the peptide used in the present invention. However, if the size is too large, production of the peptide is difficult, ease of handling is poor, and the angiogenic activity per a unit weight is thought to be small. Thus, the total number of the amino acids constituting the peptide is usually 4 to 350, preferably 4 to 50, more preferably 5 to 20, still more preferably 5 to 10, and still more preferably 6 to 10. The peptides having the same amino acid sequence as shown in any one of SEQ ID NOs: 1 to 7 and 9 to 11, except that not more than 10 other amino acids are attached to one or both termini, respectively, of the sequence are also preferred. For example, the amino acid sequence shown in SEQ ID NO: 12 or 13 is one wherein an amino acid sequence is attached to one terminal of the amino acid sequence shown in SEQ ID NO:1, and it was confirmed that both of them have high angiogenic activities. Since it was confirmed that the peptides having the amino acid sequences shown in SEQ ID NOs. 2 to 7 and 9 to 11 have angiogenesis actions in the Examples below, all of these are preferred examples.

Whether a peptide has angiogenesis action or not can be examined by embedding a microcell filled with the peptide solution in the back of a mouse, and by observing the formation of capillary blood vessels in the tissue surrounding the embedded microcell, as described in the Examples below.

The above-described peptide may easily be synthesized by a conventional method employing manual synthesis or using a commercially available peptide synthesizer. The peptides having large sizes may be produced by a conventional genetic engineering method.

The peptide may be topically administered to the tissue in which angiogenesis is desired, in the form of the peptide alone or in the form of an injection solution prepared by dissolving the peptide in physiological buffer. By topically administering the angiogenesis drug according to the present invention to the vicinity of wound or the like formed by surgery or injury by injection, application, spraying or the like, angiogenesis is accelerated and so the healing of the wound is accelerated. The peptide concentration in the peptide solution used for the injection, application, spraying or the like is not restricted, and usually about 1 to 10 µg (microgram)/mL. The dose of administration may appropriately be selected depending on the size and depth of the wound or the like, and may be one with which the wound is entirely covered with the peptide solution. The peptide solution may be administered once to several times per one to several days until the wound is cured. The injection solution may contain various components such as antiseptic and antiphlogistic/analgesic agent, which are normally contained in the therapeutic drugs for wounds.

Angiogenesis may also be accelerated by binding the peptide to a carrier and embedding the carrier to which the peptide is bound in the body. By this, it is possible to have the drug selectively act on the site at which angiogenesis is required because the peptide is fixed to the carrier, so that it is highly hopeful as a new DDS (drug delivery system). By topically administering the angiogenesis drug according to the present invention to the site at which a biological material is transplanted, by injection, application, spraying or the like, angiogenesis is accelerated and so the healing after the surgery is accelerated. The carrier used herein is not restricted, and examples of the carrier include resins used as substitute bones, substitute teeth and artificial organs, and biopolymers such as proteins. By binding the above-described peptide to a resin, angiogenesis is accelerated in the tissue contacting the resin, when the resin is embedded in the body, so that the compatibility between the resin and the body is improved. In a more preferred mode, a protein (unless otherwise mentioned, the term "protein" include protein-containing complexes such as glycoproteins and lipoproteins) may be used as the carrier.

The protein used as the carrier may be any protein having biocompatibility, and may preferably be a cell-adhesive protein in order to attain good adhesion with the tissue. Preferred examples of the cell-adhesive proteins include collagen (gelatin), fibronectin, vitronectin and laminin as well as partial hydrolysis products thereof, although the proteins are not restricted thereto. These proteins may preferably be purified proteins from which allergens are removed, from the viewpoint of prevention of allergic reactions. For example, as for collagen, although various collagens obtained from animals are commercially available, they are not preferred for clinical use because the purities are low, contain allergens and have low reproducibilities. Gelatin for clinical use, obtained by partially hydrolyzing collagen originated from an animal, from which allergens are removed, is commercially available, and such a purified collagen or partial hydrolysis products thereof may preferably be used.

The amount of the peptide to be bound to the carrier is not restricted, and may be appropriately selected. The weight ratio of the carrier to the peptide (carrier:peptide) is usually about 100:1 to 1:1, preferably about 20:1 to 5:1.

The bond between the carrier and the peptide is preferably covalent bond. The binding may easily be attained by, for example, binding the amino group at the N-terminal of the peptide and an arbitrary amino group in the carrier using a crosslinking agent such as glutaraldehyde, and an example of the method for the binding is described in detail in the Examples below. In cases where the peptide is bound to a resin contained in the artificial organ or the like, a monomer having a group which may be used for the binding with the peptide, such as amino group, is copolymerized in the resin, and this amino group or the like and the amino group at the N-terminal of the peptide may be bound. It is also preferred to employ a peptide having the amino acid sequence shown in SEQ ID NO:1 or a modified peptide having the same amino acid sequence as shown in SEQ ID NO:1 except that a part of the amino acids is substituted or deleted, to which other peptide(s) having arbitrary sequence(s) are attached at its one or both termini, and to use the arbitrary peptide for the binding with the carrier.

The carrier to which the peptide is immobilized may be applied or sprayed. Alternatively, it may be implanted in the body as it is. In cases where a cell-adhesive protein is used as the carrier, the peptide-bound carrier may be used as surgical suture, various orthopedic materials, adhesion-accelerating agent for wounds, individually or in combination with other drug components. Further, the carrier protein to which the peptide is bound may be mixed with apatite carbonate or with other materials such as cell-adhesive proteins to which the peptide according to the present invention is not bound, and the mixture may be used as substitute bone or the like. In this case, the amount of the peptide contained in the final biomaterial such as the substitute bone or the like is not restricted, and usually about 0.1 mg to 10 mg per 100 g of the biological material.

Since the peptides used in the present invention are constituted by the amino acids constituting the naturally occurring proteins, and so finally decomposed to the amino acids by the action of endogenous peptidase, they are highly safe. In fact, in the in vivo experiments using mice described in the Examples below, toxicity was not observed at all. This means that toxicity was not observed at the dose at which the drug exhibited its pharmacological effect.

EXAMPLES

The present invention will now be described concretely by way of examples thereof.

Example 1

Synthesis of Peptides

The heptapeptide (designated AGP (abbreviation of angiogenic peptide)) having the amino acid sequence shown in SEQ ID NO:1 was synthesized with a high efficiency solid-phase method (K. Nokihara et al., Innovation and Perspectives in Solid-Phase Synthesis 1992, ed., R. Epton, Intercept Limited, Andover, UK, 445–448, 1992, Design and Applications of a Novel Simultaneous Multiple Solid-Phase Peptide Synthesizer; Kiyoshi NOKIHARA, Journal of Synthetic Organic Chemistry Japan, 52, 347–358, 1994, "Highly Efficient Peptide Synthesis: Automated Simultaneous Multiple Solid-Phase Synthesis and Peptide Library") based on Fmoc chemistry by using an automatic peptide synthesizer. The resulted peptide was characterized by liquid chromatography-mass spectrometry (LCMS) system to confirm that the peptide was highly homogeneous (single component, matched to a theoretical mass value).

Example 2

Angiogenenic Action in Three-Dimensionally Cultured Vascular Endothelial Tissue

Rat vascular endothelial cells were three-dimensionally cultured in the presence of AGP synthesized in Example 1. As the cells, transformed rat lung endothelial cells (TR-LECs) were used. TRLECs were placed in a collagen I layer mixed with the peptide solution, which contained 10 µg/ml of AGP, and cultured in a carbon dioxide gas incubator for 14 days. Control experiments were carried out in the absence of a factor. And positive control experiments were performed in the presence of VEGF, which is known as a potent angiogenesis factor.

Fourteen days later, the cultured cells were observed with a microscope. No tubes were detected in the control at all. In the presence of AGP or VEGF, endothelial cells were adhered each other and arranged in the tube-like structure. The tubes were observed with an electron microscope at a magnification of ×7000. It was observed that a plurality of microvilli were found on the inner surfaces of the tubes. The sites of adhesion between the vascular endothelial cells surrounding the tubes were observed at a magnification of ×15,000. Tight junction formation was observed where the endothelial cells were firmly bound. These observations indicate that the endothelial cells acquired polarity and formed tubes. The polarity means that a cell develops regions having different functions such as head and tail. No polarity is given to the endothelial cells when the endothelial cells are cultured in a usual way, and so no tubes are formed. Therefore, it is indicated that the tube formation was induced by the peptide. The lengths of the tubes formed in the presence of AGP were significantly longer than those formed in the presence of VEGF. By these results, it was confirmed that AGP has an action to adhere the cultured vascular endothelial cells in the tissue constituted by the cultured vascular endothelial cells, and to form tubes therebetween (In the body, the tubes become blood vessels).

Example 3

Comparative Example 1

Angiogenesis Action in vivo Examined by DAS Assay

A solution containing the peptide at a concentration of 10 μg/ml in DMEM (Dulbecco's modified Eagle medium) used as a cell culture medium was prepared. A microcell which was a cylinder having a diameter of 0.45 mm of which upper and lower ends were covered with Millipore filter was embedded in the back of each mouse, and then the above-mentioned peptide solution of AGP or of VEGF was injected into the microcell. As a control, phosphate buffered saline (PBS) alone which did not contain the peptide was also injected into the microcell (Comparative Example 1). Five days later, the state of the vicinity of the microcell was observed with a microscope.

As a result, a number of branched capillary blood vessels were formed in the tissue contacting the microcell into which the AGP solution was injected. On the other hand, formation of the capillary blood vessels was not observed at all in Comparative Example 1 (control) wherein PBS alone was administered. These results can be expressed in terms of magnitude. The magnitude of AGP was 5 (magnitude 5 is hereinafter referred to as "M5"), that of the control was M0, and that of the angiogenesis protein VEGF used for comparison was M3. The magnitude indicates the number of newly formed spiral blood vessels, and M0 means that the number is 0, M1 means 1 to 10, M2 means 11 to 20, M3 means 21 to 30, M4 means 31 to 40, M5 means 41 to 50 and M6 means 51 or more. Thus, the larger the magnitude M, the higher the angiogenic activity. From the above-described results, strong (prominent) angiogenesis action in vivo of AGP was confirmed.

Examples 4 to 9

Comparative Example 2

Totally seven types of heptapeptide (SEQ ID NOs:2–8), each of which had the same amino acid sequence as AGP except that one of the 7 amino acids was substituted by alanine were synthesized as in Example 1. Each of the heptapeptide was tested for the angiogenesis action in the body of mice by the DAS assay described in Example 3.

As a result, angiogenenic activity for forming spiral blood vessels of the peptide (SEQ ID NO:2, Comparative Example 2) wherein the fourth amino acid tyrosine was substituted by alanine was not observed at all as in Comparative Example 1. However, with other peptides (SEQ ID NOs:2–7, Examples 4 to 9), new blood vessels were formed in the number comparable to or more than that in the case of AGP, so that clear angiogenesis actions were observed. The abilities of angiogenesis in terms of magnitude M were: control (no peptide) (M0), AGP(M5), AGP1(M5), AGP2(M3), AGP3(M2), AGP4(M0), AGP5(M3), AGP6(M4) and AGP7 (M6). Here, AGP1 means the peptide wherein the first amino acid was substituted by Ala, . . . and AGP7 means the peptide wherein the seventh amino acid was substituted by Ala. The angiogenesis magnitude is shown in parentheses. The above-described results indicate that at least the N-terminal and C-terminal are not necessary for the angiogenesis action. Thus, it was proved that the angiogenesis action is not impaired even when the N-terminal or C-terminal is used as the binding site for binding the peptide to a carrier.

Example 10

Binding of Peptide to Carrier Protein

As the carrier protein, FreAlagin AD type (commercially available gelatin from Miyagi Chemical Industries, Ltd., molecular weight: 2000 to 20,000), obtained by partially hydrolyzing collagen originated from an animal and removing allergens was used. FreAlagin AD type has been permitted to use clinically.

In 2.5 mL MilliQ water, 100 mg of FreAlagin AD (carrier protein) was dissolved. In 1 mL of 0.1M phosphate buffer (pH 7.0), 1.20 to 1.32 mg of AGP was dissolved, and the solution was added to the carrier protein while cooling the mixture in ice. Glutaraldehyde (25% solution) was 10-fold diluted with 0.1M phosphate buffer (pH7.0)), and 0.15 mL aliquot thereof was added dropwise to the mixture at 4° C., and the resulted reaction mixture was stirred at 4° C. for 3 to 4 hours. By this, the amino group at the N-terminal of AGP and an amino group of the carrier protein was covalently bound.

Complete immobilization was confirmed by thin layer chromatography (TLC) based on disappearance of the materials. The reaction mixture was desalted with G10 column (Pharmacia) using 5% acetic acid as an eluent. The main peak was freeze-dried to obtain the immobilized product substantially quantitatively.

Example 11

Angiogenesis Action of AGP-Bound Gelatin in Three-dimensionally Cultured Vascular Endothelial Tissue Rat vascular endothelial cells were three-dimensionally cultured in the presence of AGP-bound gelatin synthesized in Example 10. As the cells, transformed rat lung endothelial cells (TRLECs) were used. Peptide AGP-bound gelatin (conjugate) and collagen type I were mixed at a ratio of 1:10, and TRLECs were placed in a layer containing the conjugate-collagen mixture solution, having a final concentration of 10 μg (microgram/ml) and cultured in a carbon dioxide gas incubator for 14 days. Control experiments were carried out in the absence of a factor, and in the presence of VEGF known as an angiogenesis factor.

Fourteen days later, the cultured cells were observed with a microscope. No tube formations were detected in the control at all. In the presence of AGP conjugate or VEGF, endothelial cells were adhered each other and arranged in the tube-like structure. The tubes were observed with an electron microscope at a magnification of ×7000. It was observed that a plurality of microvilli were formed on the inner surfaces of the tubes. The sites of adhesion between the vascular endothelial cells surrounding the tubes were observed at a magnification of ×15,000. Tight junction formation was observed where the endothelial cells were firmly bound. These observations indicate that the endothelial cells acquired polarity and formed tubes. The lengths of the tubes formed in the presence of AGP conjugate were significantly longer than those formed in the presence of VEGF. By these results, it was confirmed that AGP conjugate has an action to adhere the cultured vascular endothelial cells in the tissue constituted by the cultured vascular endothelial cells, and to form tubes therebetween (In the body, the tubes become blood vessels).

Example 11

Comparative Example 3

Angiogenesis Action in vivo Examined by DAS Assay

The AGP conjugate (prepared in Example 10) having a concentration of 100 μg/ml was dissolved in collagen I at a ratio of 1:10 to obtain a peptide-bound gelatin collagen mixture solution having a concentration of 10 μg/ml. A microcell which was a cylinder having a diameter of 0.45 mm of which upper and lower ends were covered with Millipore filter was embedded in the back of each mouse, and then the above-mentioned peptide solution of AGP conjugate or of VEGF was injected into the microcell. As a control, phosphate buffered saline (PBS) alone which did not contain the peptide was also injected into the microcell (Comparative Example 3). Five days later, the state of the vicinity of the microcell was observed with a microscope.

As a result, a number of branched capillary blood vessels were formed in the tissue contacting the microcell into which the AGP conjugate solution was injected. On the other hand, formation of the capillary blood vessels was not observed at all in Comparative Example 3 wherein PBS alone was administered. The angiogenesis magnitude of the control was M0, that of AGP was M5 and that of VEGF was M3. From these results, the angiogenesis action of the AGP conjugate in vivo was confirmed.

Examples 12–21

Comparative Examples 4–7

Peptides having the amino acid sequences of 9 to 22 were prepared and subjected to DAS assay as in Example 3. The results are shown in Table 1 below.

TABLE 1

| Examples | SEQ ID NO: | Sequence | Angiogenesis Magnitude |
|---|---|---|---|
| Example 12 | 9 | SVVFGLR | M6 |
| Example 13 | 10 | SVVYGL | M5 |
| Example 14 | 11 | VVYGLR | M5 |
| Example 15 | 12 | SVVYGLRG | M4–5 |
| Example 16 | 13 | GRGDSVVYGLR | M4–5 |
| Example 17 | 14 | RGDSVVYG | M2–3 |
| Example 18 | 15 | SVV yGLR (y = D Tyr) | M2 |
| Example 19 | 16 | SVVWGLR | M3 |
| Example 20 | 17 | SVVYG | M2 |
| Example 21 | 18 | SVVY | M1 |
| Comparative Example 4 | 19 | SVV | M0 |
| Comparative Example 5 | 20 | VYGLR | M0 |
| Comparative Example 6 | 21 | YGLR | M0 |
| Comparative Example 7 | 22 | GLR | M0 |

Note:
The symbol "y" in Example 18 (SEQ ID NO:15) denotes D-tyrosine.

The above-described results show that the peptides having amino acid sequences shown in SEQ ID NOs: 9 to 11 have very high angiogenic activities, and especially the peptide having the amino acid sequence shown in SEQ ID NO: 9 has an especially high angiogenic activity. It was also proved that the peptides in which peptides having other amino acid sequences are attached to the N-terminal or C-terminal of the amino acid sequence shown in SEQ ID NO:1 also have high angiogenic activities.

INDUSTRIAL AVAILABILITY

The angiogenesis drugs according to the present invention have strong angiogenesis actions and are useful for implantation of biological substitute materials such as artificial bones and artificial organs in the body, and for tissue reconstruction. The angiogenesis drugs are also useful for therapies of ischemic diseases such as myocardial infarction, cerebral infarction and obstructive aortic sclerosis, which occupies a large portion of lifestyle diseases.

The invention claimed is:

1. A method for stimulating angiogenesis, said method comprising administering an angiogenesis to the site of a patient, at which it is desired to stimulate angiogenesis;

Wherein, said angiogenesis drug comprises as an effective ingredient a peptide having the amino acid sequence shown in SEQ ID NO: 1 or a peptide having the same amino acid sequence as shown in SEQ ID NO: 1 except that 1 to 3 amino acids are substituted, and/or 1 or 2 amino acids located at one or both termini, respectively, of said sequence are deleted, and/or that other amino acid(s) is (are) attached to one or both termini of said sequence, which has an angiogenesis action.

2. The method according to claim 1, wherein the effective ingredient comprises a peptide having the amino acid sequence shown in SEQ ID NO: 1 or a peptide having the same amino acid sequence as shown in SEQ ID NO: 1 except that 1 or 2 amino acids are substituted (with the proviso that the fourth amino acid tyrosine residue is tyrosine residue or an amino acid having an aromatic ring in its side chain), and/or that one amino acid located at one or both termini, respectively, of said sequence is deleted, and/or other amino acid(s) is(are) attached to one or both termini of said sequence, which has an angiogenesis action.

3. The method according to claim 2, wherein said amino acid having an aromatic ring in its side chain is phenylalanine or a chemically modified phenylalanine having one or more substituents on its benzene ring.

4. The method according to claim 1, wherein the effective ingredient comprises a peptide having the amino acid sequence shown in SEQ ID NO: 9 or a peptide having the same amino acid sequence as shown in SEQ ID NO: 9 except that one amino acid located at one or both termini, respectively, of said sequence is deleted, or that other amino acid(s) is (are) attached to one or both termini of said peptide having the amino acid sequence shown in SEQ ID NO: 9 or to one or both termini of said peptide having the same amino acid sequence as shown in SEQ ID NO: 9 except that one amino acid located at one or both termini, respectively, of said sequence is deleted, which has an angiogenesis action.

5. The method according to claim 2, wherein the effective ingredient comprises a peptide having the amino acid sequence shown in any one of SEQ ID NOS: 1 to 7, or a peptide having the same amino acid sequence as shown in any one of SEQ ID NOS: 1 to 7, except that other amino acid(s) is (are) attached to one or both termini of said sequence, which has an angiogenesis action.

6. The method according to claim 2, wherein the effective ingredient comprises a peptide having the amino acid sequence shown in any one of SEQ ID NOS: 9 to 11, or a peptide having the same amino acid sequence as shown in any one of SEQ ID NOS: 9 to 11, except that other amino acid(s) is (are) attached to one or both termini of said amino acid sequence, which has an angiogenesis action.

7. The method according to claim 6, wherein the effective ingredient comprises a peptide having the amino acid sequence shown in SEQ ID NO: 9, or a peptide having the same amino acid sequence as shown in SEQ ID NO: 9, except that other amino acid(s) is (are) attached to one or both termini of said sequence, which has an angiogenesis action.

8. The method according to claim 1, wherein the total number of amino acid residues in said effective ingredient is 4 to 350.

9. The method according to claim 8, wherein the total number of amino acid residues in said effective ingredient is 4 to 50.

10. The method according to claim 9, wherein the total number of amino acid residues in said effective ingredient is 5 to 20.

11. The method according to claim 5, wherein the effective ingredient comprises a peptide having the amino acid sequence shown in any one of SEQ ID NOS: 1 to 7, or a peptide having the same amino acid sequence as shown in any one of SEQ ID NOS: 1 to 7, except that not more than 10 other amino acids are attached to one or both termini, respectively, of said sequence.

12. The method according to claim 11, wherein said effective ingredient has the amino acid sequence shown in any one of SEQ ID NOS: 1 to 7.

13. The method according to claim 12, wherein the effective ingredient comprises a peptide having the amino acid sequence shown in any one of SEQ ID NOS: 10 or 11, or a peptide having the same amino acid sequence as shown in any one of SEQ ID NOS: 10 or 11, except that not more than 10 other amino acids are attached to one or both termini, respectively, of said sequence.

14. The method according to claim 12, wherein said peptide has the amino acid sequence shown in any one of SEQ ID NOS: 10 or 11.

15. The method according to claim 1, wherein said effective ingredient is bound to a carrier.

16. The method according to claim 15, wherein said carrier is a protein.

17. The method according to claim 16, wherein said protein is a cell-adhesive protein.

18. The method according to claim 17, wherein said cell-adhesive protein is collagen or a partially hydrolyzed product thereof.

19. The method according to claim 1, wherein the effective ingredient comprises a peptide having the amino acid sequence of SEQ ID No: 9.

20. The method of claim 19, wherein said peptide has not more than 10 other amino acids attached to one or both termini of said sequence.

* * * * *